Figure 1:
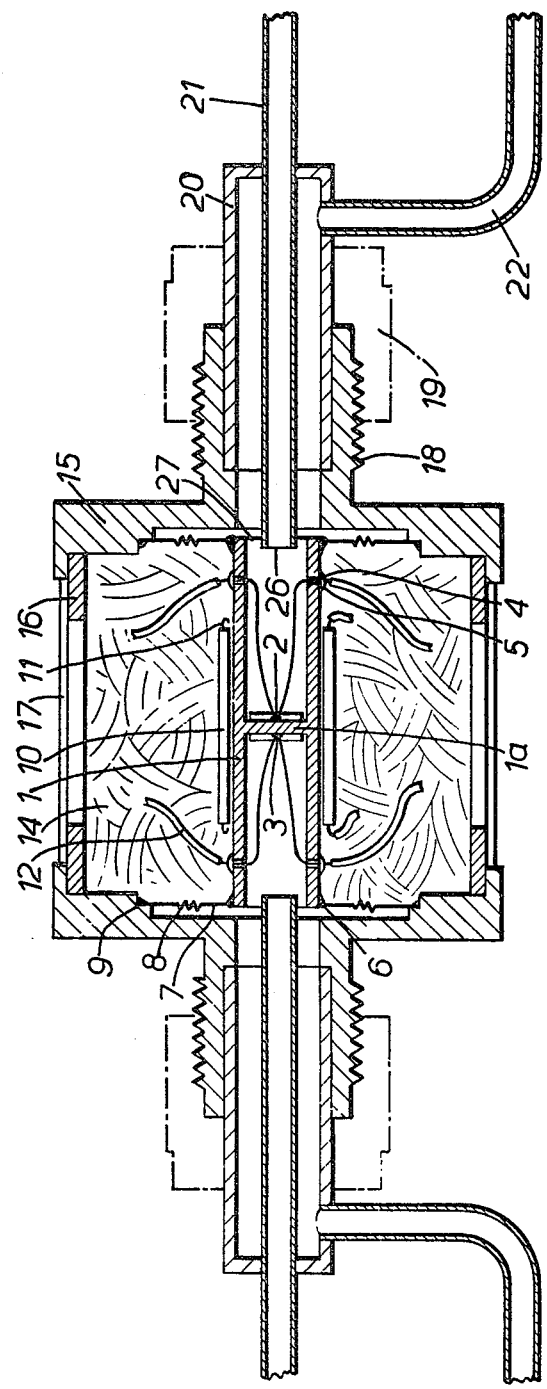

United States Patent [19]

Kocache et al.

[11] 4,333,811

[45] Jun. 8, 1982

[54] DEVICE FOR MONITORING A COMPONENT IN A FLUID MIXTURE

[75] Inventors: Riad M. A. Kocache; Danny F. Holman, both of Crowborough, England

[73] Assignee: Sybron Corporation, Rochester, N.Y.

[21] Appl. No.: 161,449

[22] Filed: Jun. 20, 1980

[30] Foreign Application Priority Data

Jun. 21, 1979 [GB] United Kingdom ............... 7921718

[51] Int. Cl.³ ........................................... G01N 27/58
[52] U.S. Cl. ................................................ 204/195 S
[58] Field of Search ................................... 204/195 S

[56] References Cited

U.S. PATENT DOCUMENTS

| | | | |
|---|---|---|---|
| 3,546,086 | 12/1970 | Sayles | 204/195 S |
| 3,691,023 | 9/1972 | Ruka et al. | 204/195 S X |
| 3,869,370 | 3/1975 | Sayles | 204/195 S |
| 4,088,543 | 5/1978 | Ruka | 204/195 S X |
| 4,238,308 | 12/1980 | Kocache et al. | 204/195 S |

Primary Examiner—Kyle L. Howell
Assistant Examiner—Joseph W. Roskos
Attorney, Agent, or Firm—Theodore B. Roessel; Joseph C. MacKenzie

[57] ABSTRACT

A device for monitoring a component in a fluid mixture includes a tube 1, the bore of which is divided into two chambers by a disc of solid electrolyte 1a. The electrolyte is chosen to have a conducting ion related to the component to be measured. Suspension device in the form of two resilient diaphragms 7 suspend the tube within a housing including a frame member 16 and end caps 15. Each of the diaphragms is sealed at its interface 9 with the housing, and at its interface 6 with an end of the tube. Heater 10, 11 are provided to alter the temperature of the component in each chamber and inlet 21 and outlet 22 allow fluid to enter and leave the chambers.

The e.m.f. between electrodes 2 is monitored and information about the fluid mixture can be obtained depending on the temperature of the mixture sensed by a thermocouple arrangement 3.

11 Claims, 5 Drawing Figures

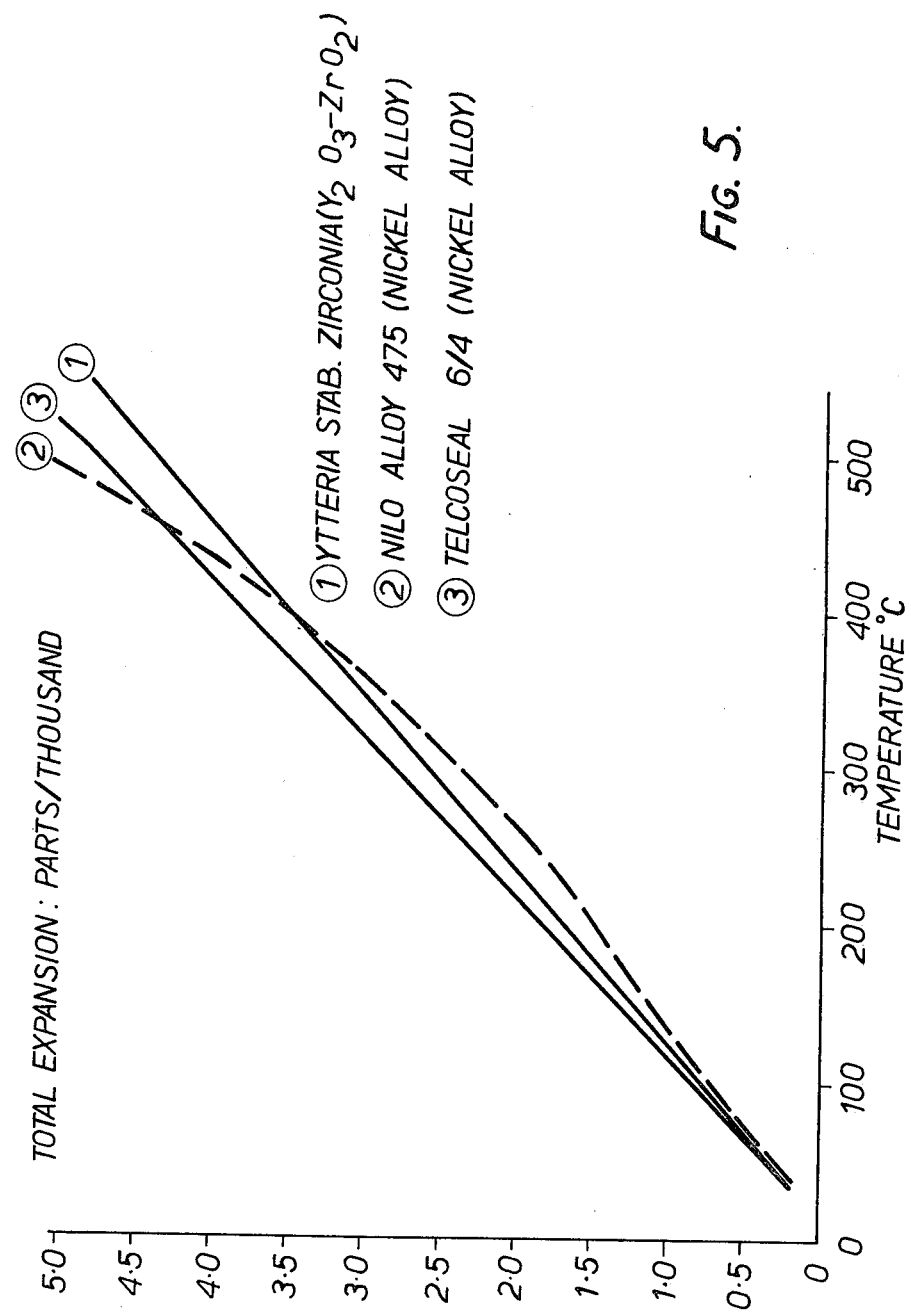

DEVICE FOR MONITORING A COMPONENT IN A FLUID MIXTURE

The present invention relates to a device for monitoring a component in a fluid mixture and more particularly to such a device which utilises a solid electrolyte.

Investigations into the properties of solid electrolytes have been undertaken since the last century. It has been proposed to utilise high temperature concentration cells using solid electrolytes which measure the e.m.f. produced by reactions between gases such as CO and $O_2$ on one side of the cell, keeping a constant $O_2$ concentration on the other side. This enables the calculation of thermodynamic data for the gas at different temperatures. It has been found that the e.m.f. is proportional to the chemical potential of the component under equilibrium conditions which in turn is related to its concentration or its partial pressure in gases.

By choosing an electrolyte system which is compatible with the fluid mixture to be monitored, such cells can be utilised in a variety of modes:

(a) as concentration cells—if the concentration of a component on one side (reference) is known, the output e.m.f. will be related to the concentration of that component on the other side; such a cell may form part of a concentration meter, or provide thermodynamic data etc., (b) as fuel cells for electric power generation, and (c) as pumps—if an electric current is passed through the electrolyte with the appropriate component having differing concentrations on either side, a transfer of part of the component from one side to the other is effected, the extent of which is primarily determined by the amount of current passed.

A problem with previously proposed designs is fragility leading to possible fracture of the structure, due mainly to the use of large size ceramic units with low thermal conductivity. A further problem is to effect a good seal between the cell and the inlet means through which the fluid mixture is introduced into the cell.

The present invention provides a device for monitoring a component in a fluid mixture comprising a tube, the bore of which is divided into two chambers by a disc of solid electrolyte having a conducting ion related to the component to be monitored, the disc being provided with electrodes on its opposed faces, the device further comprising a housing within which said tube is disposed, and suspension means for resiliently suspending said tube within said housing.

In the preferred embodiment, the suspension means comprises two resilient diaphragms suspending the tube within the housing, each of the diaphragms being sealed at the interface between the diaphragm and the housing, and also at the interface between the diaphragm and a respective end of the tube.

The device preferably includes heating means disposed about the tube in such a way as to provide equal temperatures on either side of the electrolyte disc.

In the preferred embodiment, the electrolyte disc is disposed substantially mid-way along the length of the tube thereby providing a generally symmetrical structure.

Figure 2:
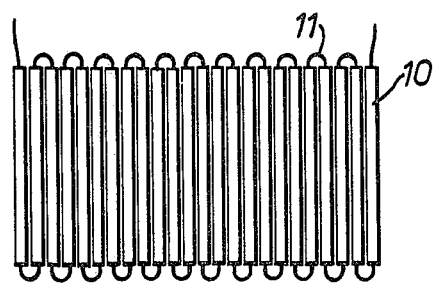
Figure 3:
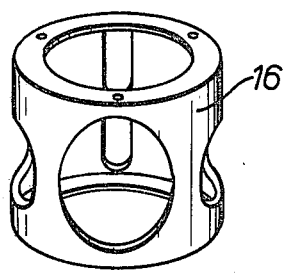
Figure 4:
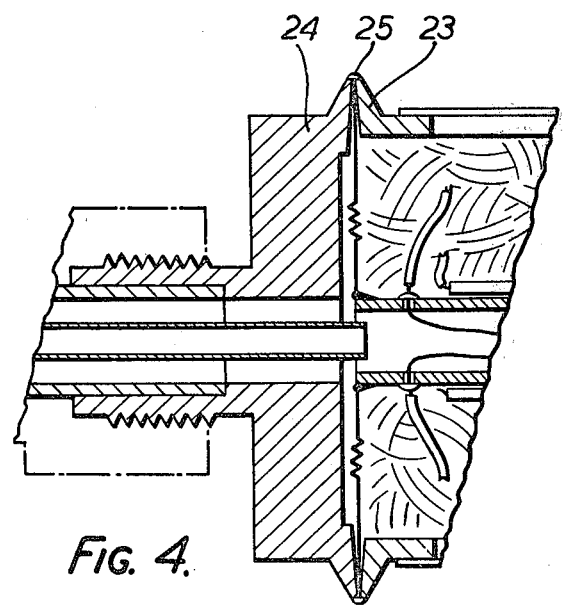

In order that the present invention may be more readily understood, embodiments thereof will now be described, by way of example, with reference to the accompanying drawings, in which:

FIG. 1 shows a section through the centre of a device in accordance with one embodiment of the invention, FIG. 2 shows heating means which form part of the device of FIG. 1, FIG. 3 shows a perspective view of another part of the device of FIG. 1, FIG. 4 shows a section through the centre of a portion of a second embodiment, and FIG. 5 is a graphical representation showing parameters of materials which may be used in the device.

The basic construction of one embodiment of the device is shown in FIG. 1. A tube 1 is shown as being formed integrally with a small and thin internally disposed disc 1a, and in such an arrangement, both tube 1 and disc 1a will be formed of a solid electrolyte material. Such an arrangement may, for example, be constructed by means of injection moulding. This is the presently preferred arrangement, but a tube having a separate disc sealed within its interior can be utilised as an alternative. The electrolyte disc 1a is arranged to have a high ionic conductivity appropriate to the measurement required and a low electronic conductivity, and separates two chambers, one being a reference chamber and the other a sample chamber. The chambers are interchangeable due to the symmetry of the design. Each side of the disc 1a is provided with an electrode 2 having an active area in the form of a layer of porous electronically conducting powder, such as platinum powder. This layer can be applied by sputtering or by using a commercial paste. Each electrode 2 also forms part of a thermocouple 3 consisting of very fine wire embedded adjacent the centre of the respective face of the disc 1a. In many cases it will be found that the temperature on each face of the disc is nearly identical in which case one thermocouple suffices and only a single electrical conductor wire is needed on the opposite face. The e.m.f. across the disc is measured using one of the thermocouple wires from each electrode 2, the selected wires being made of the same material.

The thermocouple wires are brought through the body of the tube 1 via small holes with insulators 4 of suitable material such as alumina inserted to isolate the wire from the tube. The tube holes are then sealed, for example, with a suitable glass composition 5.

The tube 1 is arranged to be disposed within a housing which includes a frame member 16 and two end caps 15 attached to the ends of the frame member 16. The tube 1 is resiliently suspended within the housing by suspension means in the form of two diaphragms 7 attached to the housing, the diaphragms being composed of a material having suitable corrosion resistance to the fluid being monitored and a temperature coefficient which is matched to the material used for the tube 1. Each diaphragm 7 is preferably provided with corrugations 8 for providing a greater degree of resilience and is sealed at the interface 6 with the tube 1 and also at the interface 9 with the end cap 15 of the housing. A suitable thickness of the diaphragm is about 0.005" (0.13 mm.) and this provides a good compromise between strength and resilience.

The seal at the tube interface 6 may be effected using a suitable solder glass or by vacuum brasing after the ends of the tube have been metallised with a suitable material such as platinum. The metallising may be effected by firing platinum paste at the ends of the tube. The diaphragm 7 can be formed of a high temperature steel such as 310 steel having equivalents in U.S.

(A1S1), Germany (X15CrNiSi 25-20), France (Z15CNS 25-20) and Sweden (2361); or preferably the material used can be a nickel alloy such as those manufactured by Henry Wiggin & Co. under the codes Nilo 51 or Nilo 475".

The seal at the interface 9 with the end cap can be effected by means of argon arc welding or vacuum brazing. Once the seals have been made, the tube 1 is effectively suspended between the two resilient diaphragms 7, and this greatly reduces the chance of breakage of the tube, particularly when it is formed integrally with the disc 1a and is therefore of a solid electrolyte ceramic material. At the same time, a very good seal is obtained within the device, and this substantially overcomes the problem of leakages, which is a major disadvantage of some previously proposed arrangements.

Heating means are preferably provided as shown to produce a uniform temperature distribution within the tube 1. Short lengths of thin insulating tubes or sleeves 10, preferably made of a ceramic such as alumina or other material whose electrical resistance stays high at high temperatures, have electric heater wire 11 threaded therethrough and are subsequently arranged adjacent each other and mutually parallel as shown in FIG. 2. The resulting arrangement is then wrapped centrally around the tube 1 and secured thereto with high temperature cement or high temperature solder glass. It has been found that using the above arrangement and the dimensions given below, the temperature difference between the active areas of the electrodes 2 may be kept to the order of one centigrade degree.

| Length of insulators 10 | 16–23 mm. |
|---|---|
| O/D of insulators 10 | 1 mm. |
| Length of tube 1 | 30 mm. |
| O/D of tube 1 | 6 mm. |
| I/D of tube 1 | 4 mm. |
| Thickness of disc 1a | <1 mm. |

The electric heater wire 11 and the wires from the thermocouple 3 are inserted in high temperature insulating sleeving 12 and are embedded within high temperature insulating loose fibres 14 which are disposed between the tube 1 and the housing for purposes of thermal insulation. The packing of the fibres 14 is not sufficiently great to counteract the suspension effect of the diaphragms.

Alternative heating means may be provided, such as heater wire wound directly on to the tube 1 in grooves provided for the purpose. However, it has been found that such an arrangement is conducive to cross-interference between the electrodes and the heater circuit, due to the comparatively lower electrical resistance at high temperatures of the tube 1 when made of solid electrolyte.

Further features of the device shown in FIG. 1 include terminations on the end caps 15 such as screw-threaded projections 18 arranged to accept fluid connectors 20 and retain the connectors in place by means of nuts (shown schematically at 19). The fluid connectors 20 include inlet and outlet means, 21 and 22 respectively, for the fluid to be monitored, and the design is preferably such that the cross-sectional area 26 of the inlet means 21 is about the same as the remaining area 27 of the tube 1. This allows the fluid in the chamber to be flushed out very quickly, e.g. within one second at flow rates of 100–200 ml/min without the need to extend the pipe of the inlet means 21 more than 1–2 mm. into the chamber.

An outer cover 17 preferably made of metal is fixed over the frame member 16 and between the end caps 15. A more detailed view of the frame member 16 is shown in FIG. 3.

FIG. 4 shows an alternative means of attaching the diaphragm to the housing. In this case, a diaphragm 25 is sandwiched between an end cap 24 and a frame member 23, the end cap and frame member having suitably mating surfaces, and being joined together and to the diaphragm 25 by argon arc welding. Other features of the device shown in FIG. 4 are similar to those shown in FIG. 1.

An alternative way of effecting the seal at the diaphragm-tube interface 6 is by means of a compression glass seal. For this method, the diaphragm material has to have specially selected thermal expansion characteristics. It is necessary for the diaphragm to expand more than the electrolyte tube 1 at the working temperature of the glass, and at lower temperatures to follow the temperature expansion characteristics of the tube material. Thus the diaphragm may be fitted over the tube at the glass working temperature, and forms a compression seal at the lower working temperatures of the device. FIG. 5 shows curves of thermal expansion characteristics of three materials, ytteria- zirconia which may be used for the electrolyte-tube, the aforementioned Nilo 475 alloy and a further nickel alloy, Telcoseal 6/4, manufactured by Telcon Metals Ltd, either of these alloys being suitable for the diaphragm.

In use, the temperature of the device may be varied by altering the current fed to the heating means. The e.m.f. across the disc 1a may be measured using the thermocouple wires attached to the electrodes 2, and the temperature may be measured using one or both thermocouples; alternatively or additionally the temperature of the heating means may be monitored by using a temperature sensor such as a further thermocouple or a resistance thermometer located adjacent the heating means.

The device may be used in a variety of ways, for example it may be used in the constant e.m.f. mode when a suitable reference is sealed in one chamber and a fixed e.m.f. operating point selected. The operating temperature is adjusted by a control circuit which varies the temperature until the concentration of the reference component in relation to the component being sampled produces an output across the disc which is equal to the selected e.m.f. The temperature of the disc is then related to the concentration of the sample component.

Where the device is to be used with one chamber sealed, a simpler arrangement is to omit the end cap projection 18 on the sealed reference side, together with its corresponding inlet and outlet means 21, 22. The corresponding diaphragm may then be provided without an aperture for fluid flow and a sealed chamber would be created by attaching such a diaphragm to the tube.

I claim:

1. A device for monitoring a component in a fluid mixture comprising a tube, the bore of which is divided into two chambers by a disc of solid electrolyte having a conducting ion related to the component to be monitored, the disc being provided with electrodes on its opposed faces, the device further comprising a housing within which said tube is disposed, and suspension means for resiliently suspending said tube within said housing.

2. The device according to claim 1 wherein said suspension means comprises two resilient diaphragms suspending said tube within said housing, each of said diaphragms being sealed at the interface between the diaphragm and said housing, and at the interface between the diaphragm and a respective end of said tube.

3. The device according to claim 2 wherein said housing comprises a frame member and two end members, each of the latter being fixedly attached to a respective end of said frame member, and each of the diaphragms being sandwiched between said frame member and a respective end member thereby to effect a seal.

4. The device according to claim 3 further including heating means disposed adjacent said tube for providing substantially equal temperatures on each side of the disc, said heating means comprising electrical heating wire contained in electrically insulating sleeving, said electrically insulated sleeving being disposed in thermal contact with the exterior of said tube.

5. The device according to claim 4 wherein said electrically insulating sleeving comprises a plurality of sleeves disposed adjacent the exterior of said tube, said sleeves being parallel to the axis thereof.

6. The device according to claim 2 further including heating means disposed adjacent said tube for providing substantially equal temperatures on each side of the disc, said heating means comprising electrical heating wire contained in electrically insulating sleeving, said electrically insulating sleeving being disposed in thermal contact with the exterior of said tube.

7. The device according to claim 6 wherein said electrically insulating sleeving comprises a plurality of sleeves disposed adjacent the exterior of said tube, said sleeves being parallel to the axis thereof.

8. The device according to claim 1 further including heating means disposed adjacent said tube for providing substantially equal temperatures on each side of the disc, said heating means comprising electrical heating wire contained in electrically insulating sleeving, said electrically insulated sleeving being disposed in thermal contact with the exterior of said tube.

9. The device according to claim 8 wherein said electrically insulating sleeving comprises a plurality of sleeves disposed adjacent the exterior of said tube, said sleeves being parallel to the axis thereof.

10. A device for monitoring a component in a fluid mixture comprising a tube, the bore of which is divided into two chambers by a disc of solid electrolyte having a conducting ion related to the component to be monitored, the disc being provided with electrodes on its opposed faces, the device further comprising a housing within which said tube is disposed, and including heating means disposed adjacent said tube for providing substantially equal temperatures on either side of the disc;

said heating means comprising electrical heating wire contained in a plurality of electrically insulating sleeves, said electrically insulating sleeves being disposed in thermal contact with the exterior of said tube and parallel to the axis thereof.

11. The device according to any one preceding claim, and further including temperature sensing means for providing a measure of the temperature of said disc.

* * * * *